United States Patent [19]

Imamura et al.

[11] Patent Number: 5,080,670

[45] Date of Patent: Jan. 14, 1992

[54] BIOPROSTHETIC VALVE

[75] Inventors: Eisaburo Imamura, Kunitachi; Yasuharu Noishiki, Tottori; Hitoshi Koyanagi; Teruo Miyata, both of Tokyo; Masayasu Furuse, Sagamihara, all of Japan

[73] Assignee: Koken Co., Ltd., Tokyo, Japan

[21] Appl. No.: 238,233

[22] Filed: Aug. 30, 1988

[30] Foreign Application Priority Data

Aug. 31, 1987 [JP] Japan .................. 62-215365

[51] Int. Cl.$^5$ .................. A61F 2/24
[52] U.S. Cl. .................. 623/2; 623/66
[58] Field of Search .................. 623/2

[56] References Cited

U.S. PATENT DOCUMENTS

| | | | |
|---|---|---|---|
| 4,402,697 | 9/1983 | Pollock et al. | 623/2 |
| 4,655,773 | 4/1987 | Grassi | 623/2 |
| 4,692,164 | 9/1987 | Dzemeshkevich et al. | 623/2 |
| 4,792,139 | 3/1988 | Nashef | 623/2 |

FOREIGN PATENT DOCUMENTS 0212933 3/1987 European Pat. Off. .

OTHER PUBLICATIONS

Liotta, D. et al., "Low Profile Bioprosthesis for Cardiac Valve Replacement: Early Clinical Results", Cardiovascular Diseases, Bulletin of the Texas Heart Institute, vol. 4, No. 4, pp. 371–382, 1978.
Thubrikar, M. J. et al., "Role of Mechanical Stress in Calcification of Aortic Bioprosthetic Valves", in J. Thorac Cardiovasc Surg. 86:115–125, 1983.
Ferrans, V. J. et al., "Calcific Deposits in Porcine Bioprostheses Structure and Pathogenesis", Amer. J. Cardiol. 46:721–734, 1980.
Dunn, J. M. et al., "Mechanisms of Calcification of Tissue Valves", Cardiol Clin., 3:385–396, 1985.

*Primary Examiner*—David J. Isabella
*Attorney, Agent, or Firm*—Varndell Legal Group

[57] ABSTRACT

A bioprosthetic valve made from a biological tissue containing collagen which has been cross-linked with a polyepoxy compound is disclosed. The valve has excellent biocompatibility and is durable and is free from calcification.

14 Claims, No Drawings

BIOPROSTHETIC VALVE

FIELD OF THE INVENTION

The present invention relates to a bioprosthetic valve used in valve replacement and in an artificial heart and, more particularly, to a bioprosthetic valve which is not calcified and which has excellent biocompatibility.

BACKGROUND OF THE INVENTION

From the middle of the 1950's valve replacement operations have been practiced. A wide variety of artificial valves have been developed and widely used for replacement of aortic valves, mitral valves, tricuspid valves, etc. and in artificial hearts.

Artificial valves are classified broadly into mechanoprosthetic valves and bioprosthetic valves. Mechanoprosthetic valves are further classified roughly into ball-type valves and disc-type valves, depending on the shape of moving portions. However, both types of the mechanoprosthetic valves have the following disadvantages: (1) there is not parallel flow through the bloodstream used therewith, (2) the materials which are used to make the valves readily form thrombus and deteriorate blood components to cause hemolysis, and (3) the sounds made by the valves have an adverse psychological effect on the patient.

Bioprosthetic valves which are now clinically used include porcine aortic valves treated with glutaraldehyde (hereinafter referred to as "GA") and bovine pericardia formed into the shape of a valve cusp. Such valves have an excellent antithrombogenic property. This eliminates the need to use long term warfarin anticoagulants which can possibly cause cerebral hemorrhaging. Such valves also have hemodynamic properties which provide a central blood flow characteristic. However, these valves have problems in durability in that the physical properties of the valve are such that calcium deposits on valve cusp tissues, and cracks and perforation are caused by fatiguing of valves.

Valves using biological tissues are cross-linked with GA, in order to maintain their strengths, to suppress their being absorbed into living bodies, and to reduce their antigenic property. However, the cross-linking with GA treatment inevitably makes the biological tissues stiff. The stiffened valve cusps behave differently from untreated, natural valves. Abnormal behaviors of the stiffened valve cusps become more remarkable at lower blood pressures.

About half of GA treated valves can become dysfunctional 5 to 10 years after their implantation into human bodies due to calcification and cracking. In young children showing a vigorous calcium metabolism, almost all the GA treated valves implanted are subject to calcification and become dysfunctional even earlier after the implantation, namely, after 2–6 years.

Thus, GA has various disadvantages as a cross-linking agent a biological tissue to be used as a valve in the body of humans and mammals.

The following requirements of a cross-linking agent for cross-linking biological tissue will provide an ideal bioprosthetic valve:

(1) excludes completely the antigenicity of heterologous animal tissues;

(2) prevents the invasion of calcium into biological tissues;

(3) has persistent sterilizing effects and strong resistance to infections;

(4) is free from deterioration of flexibility and elasticity of biological tissues and allows valves to behave in a manner similar to natural valves; and (5) provides valves with excellent tensile strength and torsional strength.

Ideal cross-linking agents which can be substituted for GA and satisfy the above-noted requirements have long been desired.

SUMMARY OF THE INVENTION

An object of the present invention is to provide a bioprosthetic valve which is free from calcification and which has an excellent biocompatibility.

Another object of the present invention is to provide a bioprosthetic valve comprising a biological tissue containing collagen which has been cross-linked with a polyepoxy compound.

DETAILED DESCRIPTION OF THE INVENTION

The present inventors have investigated various cross-linking agents for satisfying the above-noted requirements for an ideal bioprosthetic valve and, as a result of the finding that polyepoxy the resulting cross-linked materials have satisfactory properties and are not easily calcified, have accomplished the present invention.

Polyepoxy compounds used in the present invention are hydrophilic cross-linking agents, preferably, they are polyglycidyl ethers of polyglycerols having a polymerization degree of 1 to 3 and/or polyglycidyl ethers of polyols and, more preferably, glycerol diglycidyl ether, glycerol triglycidyl ether, diglycerol tetraglycidyl ether and ethylene glycol glycidyl ether. For a bioprosthetic material to be cross-linked in accordance with the present invention, the tissues of various mammals, such as pig, cattle, sheep and goat, can be used. When such tissues are used as they are, they can be valve tissues, such as aortic valves, pulmonary valves, mitral valves, and tricuspid valves. When valve cusps of bioprosthetic valves of the present invention are formed from membrane-like tissues, the membrane-like tissues can be materials, such as pericardium, dura mater, amnion and fascia.

The calcifying mechanism of biological tissues of heterologous animals is not completely understood at this time. It is therefore difficult to explain theoretically why no calcification occurred on the valves treated with the polyepoxy compounds and, in contrast, the GA treated valves were quickly subjected to heavy calcification, in the basic studies of the present inventors.

However, tissues cross-linked with polyepoxy compounds are hydrophilic, in contrast to tissues cross-linked with GA which are hydrophobic. The cross-linking with polyepoxy compounds maintains flexibility and elasticity of the tissues and the valves cross-linked therewith behave in a manner similar to normal, natural valves. In contrast, cross-linking with GA results in valves which have lost the elasticity of natural biological tissues. This difference results in excellent antithrombogenic properties being obtained for the tissues cross-linked with the polyepoxy compounds of the present invention when compared to cross-linking with GA.

In fact, it is well known that calcification occurs on thrombi. Calcification of bioprosthetic valves has been observed often in the portions of valves where more stress is applied. By cross-linking with glutaraldehyde, in particular, the biological tissue used for the valves is stiffened to the extent that when the valve moves in a manner to cause frequent bending, such a stiffened valve has sharply bent portions. In this case, repeated bending at the bent portions causes small cracks to occur. The collagen exposed by the cracks will induce thrombi or calcium ions will pass through openings of the cracks to cause calcification.

The present inventors have paid attention to the fact that polyepoxy compounds which are generally used in the textile industry are highly reactive to an amino group and a carboxylic group. Collagen cross-linked with the polyepoxy compounds is excellent in biocompatibility and has a flexibility close to that of biological tissues, as disclosed in Japanese Patent Application Laid-Open No. 26230/87 entitled "Cross-linked Medical Material."

The amount or percentage of the ε-amino group on the side chains of collagen which react during cross-linking can be taken as the criterion of the amount of cross-linking. According to the present invention, it has been discovered that, as compared with the GA treatment, the percentage of ε-amino group, which react is in the range of from 5 to 90%, preferably from 10 to 60%, depending on the polyepoxy compound to be used and the biological tissue to be cross-linked. The result is a cross-linked collagen having excellent physical properties, such as strength and elongation. In other words, an amount of cross-linking within the range of 5 to 90%, preferably 10 to 60%, of the collagen with the polyepoxy compound can provide a bioprosthetic valve having excellent biocompatibility, flexibility and resistance to calcification. In addition, it can be expected that the collagen cross-linked with the polyepoxy compound is considerably stable in living bodies because the cross-linked collagen has a solubility of 30% in the digestion trial with bacterial collagenase, although the solubility is a little higher than that of GA treated collagen. A particularly preferable polyepoxy compound is a glycerol polyglycidyl ether.

The blood vessels of dog, which had been cross-linked with GA and a glycerol polyglycidyl ether (GPGE), respectively, were sensitized in mice to determine antibodies with the result of no detection thereof. In addition, the blood vessel cross-linked with GPGE had an antigenic property reduced as low as that of the blood vessel cross-linked with GA.

Further, the porcine aortic valves, which had been cross linked with GPGE and GA, respectively, were subcutaneously implanted into infant rats to measure the amount of calcium deposits. The amount of calcium deposits when compared with a fresh, untreated valve (control) was more than 200 times only one month even after the implantation in the case of the GA cross-linking. In contrast, it was about two times even three months in the case of the GPGE cross-linked valve. Thus, the bioprosthetic valves comprising the biological tissues cross-linked with the polyepoxy compound have been proved to have excellent biocompatibility and physical properties and durability and are not subjected to calcification.

The bioprosthetic valves obtained by the cross-linking treatment with the polyepoxy compounds have a potential value of application as a valve substitute of an auxiliary heart which has an absolute requirement of antithrombogenic property and durability. The present invention is described in detail by way of examples which are not construed as limiting the invention in any way. In the following examples, Denacol EX-313 and Decanol EX-314 are used as the polyepoxy compounds. Denacol EX-313 and Denacol EX-314 respectively contain glycerol diglycidyl ether and glycerol triglycidyl ether as their main compound. These compounds have the following structural formulas:

glycerol diglycidyl ether, 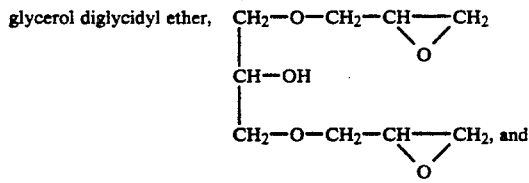

glycerol triglycidyl ether, 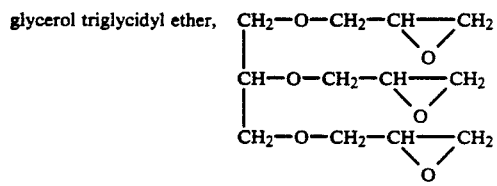

Of course, other polyepoxy compounds can be used.

EXAMPLE 1

A valve cusp was cut out of a fresh porcine aortic valve. The valve cusp was immersed in a carbonate buffer solution and then immersed in a 2% solution (pH9.0) of Denacol EX-314 (tradename of Nagase Kasei Kogyo K.K. for a glycerol polyglycidyl ether) in a phosphate buffer at 20° C. for 48 hours. The valve cusp was then washed thoroughly with water and immersed in a saline solution. The valve cusp thus treated was used for implantation experiments to evaluate the calcification preventing effects of glycerol polyglycidyl ether crosslinked animal tissue.

For comparison, a valve cusp tissue was immersed in a 0.625% solution (pH7.0) of glutaraldehyde in a phosphate buffer at 20° C. for 48 hours. Then the valve cusp was washed thoroughly with water, immersed in a saline solution, and then subject to implantation experiments.

The implantation experiments were conducted as follows: The valve cusps treated as above were implanted into the subcutaneous tissue on the backs of four-week-old rats; the implants were recovered periodically after one to three months; and the amount of calcium deposits per unit dry weight was measured by atomic absorption spectrophotometry. The results are shown in the table below. The glutaraldehyde-treated valves were subjected to calcification in amounts as much as from 90 to 170 μg/mg (average 140 μg/mg) in the same period after implanation. On the other hand, the amounts of calcium deposits of the glycerol polyglycidyl ether-treated valves were only below 1 μg per 1 mg of dry tissue one to three months after implantation and was subject to substantially no calcification when compared with 0.4 μg/mg for the fresh, untreated valve cusp tissue.

TABLE

Amount of Calcium Deposits one Valve Cusp Tissue of Porcine Aortic Valve in Subcutaneous Implantation into rat (μg/mg dry weight tissue)*

| Period After Implantation (month) | Untreated No-Implantation | Cross-linking Through Epoxy Group | Cross-linking Through Aldehyde Group |
|---|---|---|---|
| 1 | — | 0.64 ± 0.05 (n = 7) | 90.8 ± 7.9 (n = 11) |
| 2 | — | 0.94 ± 0.06 (n = 9) | 135.5 ± 10.6 (n = 16) |
| 3 | — | 0.96 ± 0.15 (n = 10) | 170.0 ± 7.1 (n = 21) |
| mean value | 0.43 ± 0.05 | 0.96 ± 0.07 (n = 25) | 140.7 ± 6.6 (n = 47) |

*Numerical valves are expressed as mean + standard error.
n = number of implantation removed.

EXAMPLE 2

The pericardium of a cattle was immersed in 0.01% aqueous ficin for 24 hours to remove proteins other than collagen, and the pericardium was then washed thoroughly with water. A 1 mm diameter stainless steel wire was formed into a frame for a bioprosthetic valve. The periphery of the frame was covered with a polyester cloth and the pericardium treated as above was used to prepare a bioprosthetic valve. The resulting valve was allowed to react by immersing it in a solution containing 10 g of Denacol EX-313 (Tradename of Nagase Kasei Kogyo K.K. for a glycerol polyglycidyl ether), 0.1 g of 2,4,6-tris (dimethylaminomethyl) phenol as a catalyst, 0.07 g of salicylic acid as a reaction accelerator, and 10 ml of ethanol dissolved in 80 ml of 0.1N NaOH at 20° C. for 24 hours. The valve so treated was then washed thoroughly with water to obtain a bioprosthetic valve according to the present invention. The resulting bioprosthetic valve was substituted for the aortic valve of a dog, and no calcification was observed on the valve after three months.

EXAMPLE 3

The aortic valve of a dog was washed with a saline solution and then immersed in 0.01% aqueous ficin for 24 hours to remove proteins other than collagen. The aortic valve was then washed thoroughly with water. Thereafter, the aortic valve was allowed to react by immersing in a solution containing 2 g of Denacol EX-314 (tradename of Nagase Kasei Kogyo K.K. for a glycerol polyglycidyl ether), 0.1 g of 2,4,6-tris(dimethylaminomethyl) phenol as a catalyst, and 0.07 g of salicylic acid as a reaction accelerator in 100 ml of 0.9% aqueous NaCl (pH9.5) at 20° C. for 24 hours. The aortic valve so treated was washed thoroughly with water to obtain a bioprosthetic valve according to the present invention, which was stored by immersion in 70% ethanol. This bioprosthetic valve was washed with a physiological sodium chloride solution, and was then implanted into the aortic valve of a dog. The implanted valve was kept open and subjected to no calcification after 6 months.

What is claimed is:

1. A bioprosthetic valve consisting essentially of an animal valve containing a crosslinked collagen/-polyepoxy compound consisting of collagen crosslinked with a polyepoxy compound to an extend of 10 to 60% with respect to an ε-amino group for increasing resistance to calcification when said bioprosthetic valve is implanted in a mammal.

2. A bioprosthetic valve according to claim 1, wherein the polyepoxy compound is a hydrophilic polyepoxy compound.

3. A bioprosthetic valve according to claim 1, wherein the polyepoxy compound is at least one of a polyglycidyl ether having a polymerization degree of from 1 to 3 and a polyglycidyl ether of a polyol selected from dihydric, trihydric and tetrahydric alcohols.

4. A bioprosthetic valve according to claim 2, wherein the polyepoxy compound is at least one of a polyglycidyl ether having a polymerization degree of from 1 to 3 and a polyglycidyl ether of a polyol selected from dihydric, trihydric and tetrahydric alcohols.

5. A bioprosthetic valve according to claim 1, wherein the valve of the animal is selected from the group consisting of porcine aortic valve, ovine aortic valve, bovine aortic valve, mitral valve, tricuspid valve and vena caval valve.

6. A bioprosthetic valve according to claim 1, wherein said valve has a valve cusp which has been formed of a membrane-like tissue.

7. A bioprosthetic valve according to claim 6, wherein the membrane-like tissue is selected from the group consisting of pericardium, dura mater, amnion of fascia.

8. A bioprosthetic valve comprising a biological tissue prepared by a method consisting of immersing an animal valve in a solution of a polyepoxy compound and crosslinking collagen in said animal valve to an extent of 10 to 60% with respect to an ε-amino group for increasing resistance to calcification when said bioprosthetic valve is implanted in a mammal.

9. A bioprosthetic valve according to claim 8, wherein the polyepoxy compound is a hydrophilic polyepoxy compound.

10. A bioprosthetic valve according to claim 8, wherein the polyepoxy compound is at least one of a polyglycidyl ether having a polymerization degree of from 1 to 3 and a polyglycidyl ether of polyol selected from dihydric, trihydric and tetrahydric alcohols.

11. A bioprosthetic valve according to claim 9, wherein the polyepoxy compound is at least one of a polyglycidyl ether having a polymerization degree of from 1 to 3 and a polyglycidyl ether of a polyol selected from dihydric, trihydric and tetrahydric alcohols.

12. A bioprosthetic valve according to claim 8, wherein the valve of the animal is selected from the group consisting of porcine aortic valve, ovine aortic valve, bovine aortic valve, mitral valve, tricuspid valve and vena caval valve.

13. A bioprosthetic valve according to claim 8, wherein said valve has a valve cusp which has been formed of a membrane-like tissue.

14. A bioprosthetic valve according to claim 13, wherein the membrane-like tissue is selected from the group consisting of pericardium, dura mater, amnion and fascia.

* * * * *